United States Patent [19]

Shiobara et al.

[11] Patent Number: 5,171,869
[45] Date of Patent: Dec. 15, 1992

[54] ALLYL OR PROPENYL GROUP-CONTAINING NAPHTHALENE DERIVATIVES

[75] Inventors: Toshio Shiobara, Annaka; Kazutoshi Tomiyoshi, Takasaki; Hisashi Shimizu; Manabu Narumi, both of Annaka, all of Japan

[73] Assignee: Shin-Etsu Chemical Company Limited, Tokyo, Japan

[21] Appl. No.: 825,222

[22] Filed: Jan. 24, 1992

[30] Foreign Application Priority Data

Jan. 25, 1991 [JP] Japan ................... 3-025757

[51] Int. Cl.$^5$ ................. C07D 303/14; C07D 303/04; C07C 39/23
[52] U.S. Cl. ...................... 549/560; 568/719
[58] Field of Search .......... 549/560; 568/719

[56] References Cited

U.S. PATENT DOCUMENTS

| 3,251,805 | 5/1966 | Schnell et al. | 568/719 |
| 3,290,269 | 12/1966 | O'Brochta | 549/560 |
| 3,631,108 | 12/1971 | Brandstrom | 549/560 |
| 4,496,773 | 1/1985 | Clouse et al. | 568/719 |
| 4,940,809 | 7/1990 | Dewhirst et al. | 549/560 |
| 4,978,810 | 12/1990 | Kanayama et al. | 568/719 |
| 5,068,293 | 11/1991 | Kaji et al. | 568/719 |

FOREIGN PATENT DOCUMENTS

| 237081 | 11/1985 | Japan | 549/560 |
| 3-000716 | 1/1991 | Japan | 549/560 |
| 3-007241 | 1/1991 | Japan | 568/719 |
| 3-027373 | 2/1991 | Japan | 549/560 |

Primary Examiner—Joseph E. Evans
Attorney, Agent, or Firm—Millen, White, Zelano and Branigan

[57] ABSTRACT

A naphthalene of the following formula (1) having at least two allyl or propenyl groups

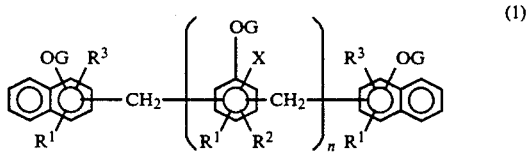

wherein each G represents a hydrogen atoms or

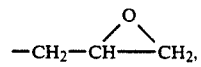

$R^1$'s independently represent a hydrogen atom or an unsubstituted or substituted monovalent hydrocarbon group having from 1 to 6 carbon atoms, $R^2$'s independently represent a hydrogen atom, an allyl group or a propenyl group, $R^3$ represents an allyl group or a propenyl group, X represents a hydrogen atom or a halogen atom, and n is an integer of from 0 to 6. The derivative is useful for modifying curable resins or resin compositions to provide cured products which have a low water absorption, high strength and a high glass transition temperature. The derivative has good working properties and a good heat resistance.

3 Claims, 3 Drawing Sheets

5,171,869

ALLYL OR PROPENYL GROUP-CONTAINING NAPHTHALENE DERIVATIVES

BACKGROUND OF THE INVENTION

1. Field of the Invention

This invention relates to naphthalene derivatives which have an allyl or propenyl group or groups and which are effective when used as an ingredient of various curable resin compositions or as a modifier for various types of curable resins. The derivatives are excellent in working properties and heat resistance and are able to provide cured product having high strength and high glass transition temperature.

2. Description of the Prior Art

Thermosetting resins have been widely used in the electric and structural fields as casting, dipping, laminating and molding materials. In recent years, there is a tendency toward severe conditions of use of the materials in these fields. Especially, importance is placed on the heat resistance and the low water absorptivity of the materials.

Known epoxy polymers which are typical of heat-resistant thermosetting resins include, for example, epoxidized phenol-novolac products (e.g. Epikote commercially available from Yuka-Shell Epoxy Co., Ltd.), epoxidize cresol-novolac products (e.g. EOCN available from Nippon Kayaku Co., Ltd.), methylenedianiline tetraepoxide, epoxidized tri- or tetra(hydroxyphenyl)alkanes and the like. There are also known as phenolic resins phenol-novolac resins, ortho-cresolnovolac resins, bis-phenol A, triphenol methane and the like resins.

Although the cured products obtained from these resins all exhibit relatively high heat resistance, the heat resistance is not always satisfactory, coupled with the disadvantage that in order to develop practical strength, heating at high temperatures over a long term is essentially required. In addition, the working properties are not satisfactory.

SUMMARY OF THE INVENTION

It is accordingly an object of the present invention to provide naphthalene derivatives which are effectively used as an ingredient for various resin compositions or as a modifier for various type of curable resins and which have good working properties and heat resistance.

It is another object of the present invention to provide thermally curable naphthalene derivatives which can yield cured products with a low water absorption and high strength when used in combination with resins having specific types of functional groups.

The above object can be achieved, according to the invention, by a naphthalene derivative of the following general formula (1) having at least two allyl or propenyl groups

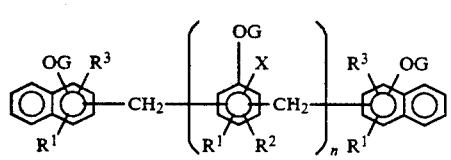
(1)

wherein each G represents a hydrogen atoms or

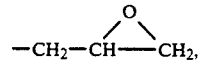

$R^1$'s independently represent a hydrogen atom or an unsubstituted or substituted monovalent hydrocarbon group having from 1 to 6 carbon atoms, $R^2$'s independently represent a hydrogen atom, an allyl group or a propenyl group, $R^3$ represents an allyl group or a propenyl group, X represents a hydrogen atom or a halogen atom, and n is an integer of from 0 to 6.

The present invention is based on the finding that when, for example, naphthol is allylated and then oligomerized or isomerized after the oligomerization and, optionally, epoxidized, there are obtained novel naphthalene derivatives having at least two allyl or propenyl group shown in formula (1). The derivatives have good working properties and moldability and can provide cured products which have good heat resistance and are not thermally deteriorated over a long term with a low water absorptivity and high strength. Therefore, the naphthalene derivatives can effectively be used as a thermosetting resin component for a semiconductor encapsulator. Further, the naphthalene derivatives having at least two allyl or propenyl groups are highly reactive with organosilicon compounds having a ≡SiH group, various types of organic compounds having a vinyl group, an epoxy group or a phenolic hydroxyl group. For instance, the naphthalene derivatives are very effective for modifying organosiloxanes, maleimide resins, epoxy resins and phenolic resins having such functional groups as mentioned above.

DETAILED DESCRIPTION AND EMBODIMENTS OF THE INVENTION

Figure 1:
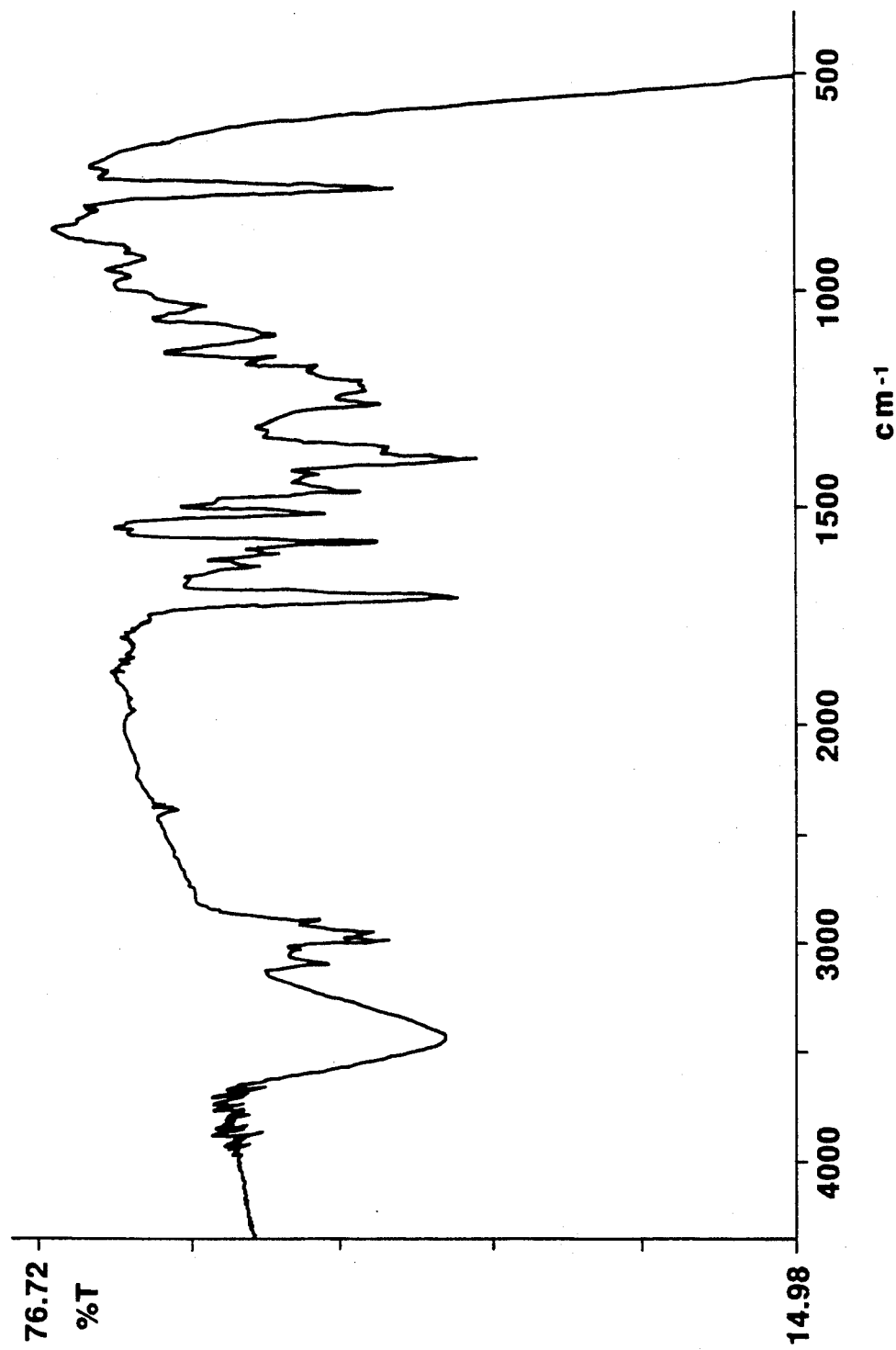
FIG. 1 is an IR absorption spectral chart of a propenyl group-containing naphthalene derivative (compound D obtained in Example 1) according to the present invention.

The novel naphthalene derivatives of the present invention are of the following general formula (1)

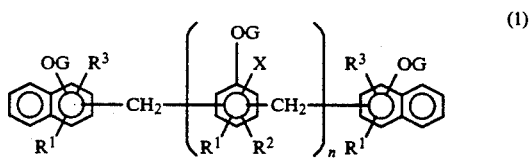
(1)

wherein each G represents a hydrogen atom or a glycidyl group, $R^1$'s independently represent a hydrogen atom or an unsubstituted or substituted monovalent hydrocarbon groups having from 1 to 6 carbon atoms, such as a methyl group, an ethyl group, a propyl group, a t-butyl group, an allyl group, a propenyl group or a phenyl group, each $R^2$ represents a hydrogen atom, an allyl group or a propenyl group, $R^3$ represents an allyl group or a propenyl group, X is a hydrogen atom or a halogen atom, and n is an integer of from 0 to 6.

Since the naphthalene derivative of the formula (1) having an allyl or propenyl group has at least two allyl or propenyl group as a functional group in the molecule, radical reaction with vinyl compounds and addition reaction with organosiloxanes having a $\equiv$SiH group and compounds having an epoxy group or a phenolic hydroxyl group are possible. Therefore, the derivatives are effective as a modifier for other epoxy resins, phenolic resins, maleimide resins and the like.

The allyl or propenyl group-containing naphthalene derivatives of the present invention can be readily prepared, for example, by allylating and then oligomerizing or oligomerizing and then isomerizing naphthol to obtain phenolic derivatives. The phenolic derivatives may be further epoxidized to obtain epoxidized derivatives.

Starting naphthol may be properly used depending on the type of intended allyl or propenyl group-containing naphthalene derivatives, including, for example, 1-naphthol.

The allylated naphthol can be obtained by subjecting naphthol to allyl etherification by any known technique, followed by Claisen rearrangement.

For obtaining a novolac derivative by oligomerization, the allylated naphthol is reacted with aldehyde compounds and then with phenol compounds such as phenol, cresol or the like by the use of known alkali or acid catalyst.

Examples of the aldehyde compounds include formaldehyde, salicyl aldehyde and the like. The amount of the aldehyde compound is not critical. Preferably, the molar ratio between the starting aldehyde compound and the phenol compound is in the range of from 0.05:1 to 1:1, more preferably from 0.11:1 to 0.7:1. If the molar ratio between the aldehyde compound and the phenol compound is less than 0.05:1, the molecular weight of the resultant oligomer may become small. When the molar ratio exceeds 1:1, gelation may take place.

The alkali catalyst includes, for example, KOH, NaOH, Ba(OH)$_2$, Mg(OH)$_2$, Ca(OH)$_2$, Sr(OH)$_2$, LiOH, (CH$_3$)$_2$NOH and the like. The acid catalyst includes, for example, hydrochloric acid, sulfuric acid, nitric acid, para-toluene-sulfonic acid, acetic acid, butyric acid, propionic acid and the like. The alkali or acid catalyst is used in a catalytically effective amount and the amount is generally in the range of from 0.5 to 2 wt % of the phenol compound.

The oligomerization should preferably be carried out in organic solvents such as toluene. Although the reaction conditions are no critical, the reaction is preferably conducted at 100° to 150° C. for 4 to 8 hours.

The isomerization of the allyl groups should preferably be effected according to an alkali isomerization technique set forth in "Journal of American Chemical Society, pp. 1709 to 1713 (1956)". By this, intended phenolic oligomerization is obtained.

It will be noted that the isomerization with an alkali may be effected after the oligomerization or the oligomerization may be effected after the isomerization.

The epoxidization can be performed by any known technique using epichlorohydrin, NaOH or the like, thereby obtaining epoxidized oligomers.

More particularly, the allyl or propenyl group-containing naphthalene derivatives of the formulas (2) to (4) can be prepared, for example, according to the following Reaction sequences I and II.

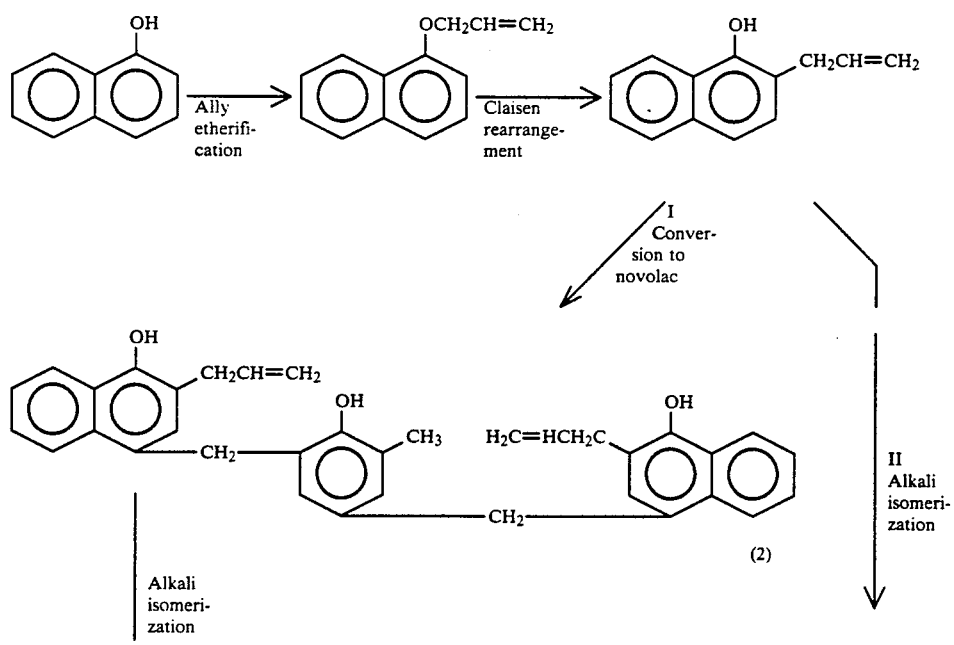

-continued

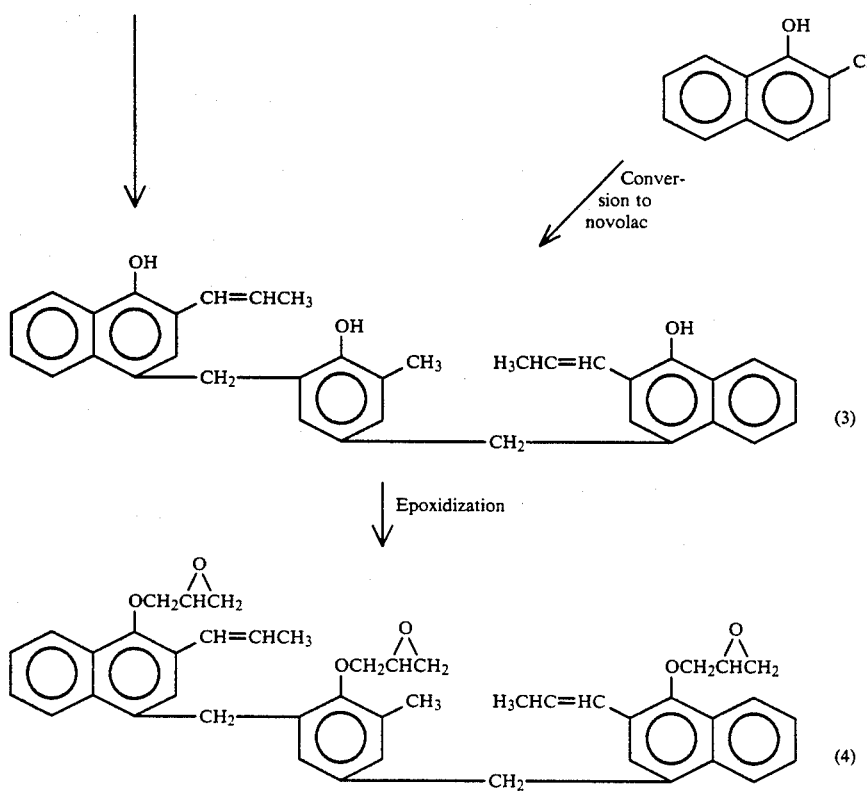

In the above reaction sequences, the allyl group-containing phenolic derivative (2) is obtained by subjecting starting 1-naphthol to allyl etherification and then to the Claisen rearrangement to obtain an allylated product, which is subsequently reacted with an aldehyde and a phenol compound in the presence of an alkali or acid catalyst to obtain a novolac product. The propenyl group-containing phenolic derivative (3) is obtained either by isomerizing the thus obtained novolac product (2) with an alkali (sequence I) or by alkali isomerizing said allylated product before conversion to a novolac product (sequence II). If necessary, the phenolic derivatives (2) and (3) may be further epoxidized to obtain epoxidized derivatives.

The present invention is described in more detail by way of example, which should not be construed as limiting the invention.

EXAMPLE 1

Preparation of Compound A 500 g of 1-naphthol was dissolved in acetone and placed along with 630 g of allyl bromide in a three liter four-necked flask equipped with a condenser, a thermometer and an agitator. While agitating, 234 g of KOH was introduced and dissolved while agitating, followed by reaction for 8 hours under reflux. After 8 hours, the mixture was filtered to remove the solvent, and the resultant cake was dissolved in 1.5 liters of methyl isobutyl ketone, followed by washing and removal of the solvent by distillation to obtain 581 g of compound A having the following structural formula at a yield of 91.1%. The compound A was identified by NMR and IR analyses.

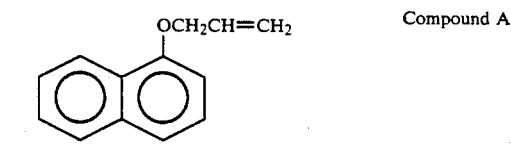

Compound A

Preparation of Compound B 580 g of Compound A was placed in a two liter four-necked flask equipped with a condenser, a thermometer and an agitator in an atmosphere of nitrogen and heated to 200° C. for reaction for 30 minutes to obtain 525.5 g of compound B having the following structural formula with a OH equivalent of 191 (theoretical: 180) at a yield of 90.6%. The compound B was identified by NMR and IR analyses.

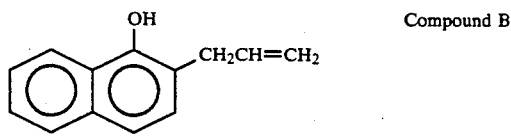

Compound B

Preparation of Compound C 444 g of Compound B and 196 g of a 37% formaldehyde aqueous solution were placed in a three liter four-necked flask equipped with a condenser, a thermometer and an agitator. While agitating, 2.6 g of KOH was added, followed by reaction for 6 hours under reflux. Thereafter, 5.8 g of oxalic acid, 126 g of toluene and 131 g of o-cresol were further added, followed by heating and dehydration for 2 hours under reflux of the toluene.

After two hours, the toluene was removed under reduced pressure, followed by further reaction at 150° C. for 1 hour. Thereafter, the reaction product was cooled and diluted with methyl isobutyl ketone, followed by washing with water and removal of the solvent by distillation to obtain 518 g of compound C with a OH equivalent of 169 (theoretical: 161) at a yield of 85.9% based on the compound B. The compound C was identified by NMR and IR analyses.

The attributions of the NMR spectra are shown below.

formula with a OH equivalent of 171 (theoretical: 161) at a yield of 97%. The compound D was identified by NMR and IR analyses. The infrared absorption spectrum chart of the compound D is shown in FIG. 1. The attributions of the NMR spectra are shown below.

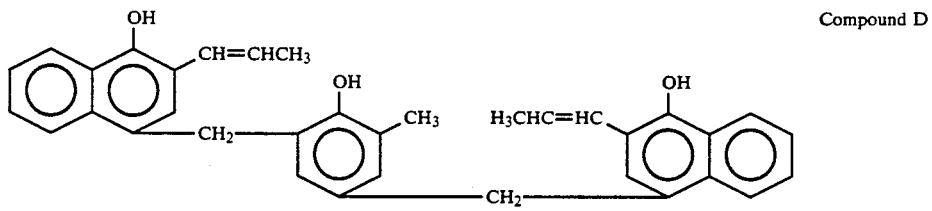

Compound D

NMR spectra (solvent: $(CD_3)_2CO$, ppm(δ)):

1.27: $-[C_6H_2]-\underset{|}{\underline{CH_3}}$, $-CH=CH-CH_3$ 3.0: $-\underline{CH_2}-$ 6.4–8.4: $-[C_{10}\underline{H}_5]-$, $[C_6\underline{H}_2]$, $-\underline{CH}=\underline{CH}-CH_3$

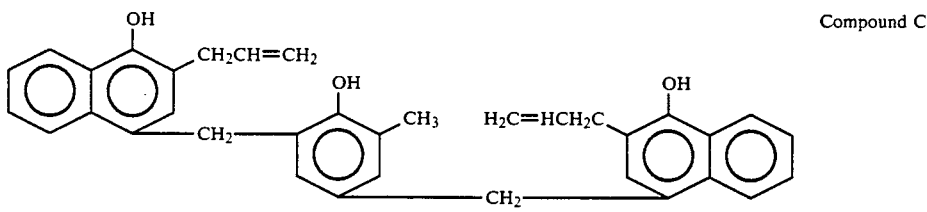

Compound C

NMR spectra (solvent: $(CD_3)_2CO$, ppm(δ)):

2.0–2.2: $[C_6H_2-]\underline{CH_3}$ 3.0–3.7: $[C_{10}H_5-\underline{CH_2}-C_6H_2]$
$[C_{10}H_5-\underline{CH_2}-CH=CH_2]$ 4.3–5.0: $CH=\underline{CH_2}$ 5.2–6.2: $-CH_2-\underline{CH}=CH_2$ 6.3–8.2: $[C_{10}\underline{H}_5]$, $[C_6\underline{H}_2]$

Preparation of Compound D 507 g of compound C, 770 g of methanol and 240 g of n-butanol were placed in a three liter four-necked flask equipped with a condenser, a thermometer and an agitator and dissolved under agitation, followed by further addition and dissolution by heating of 240 g of KOH, removal of the methanol and reaction at 110° to 120° C. for 6 hours. After 6 hours, one liter of methyl isobutyl ketone was placed, followed by neutralization with hydrochloric acid and removal of the solvent by distillation to obtain 492 g of compound D of the following

Figure 2:
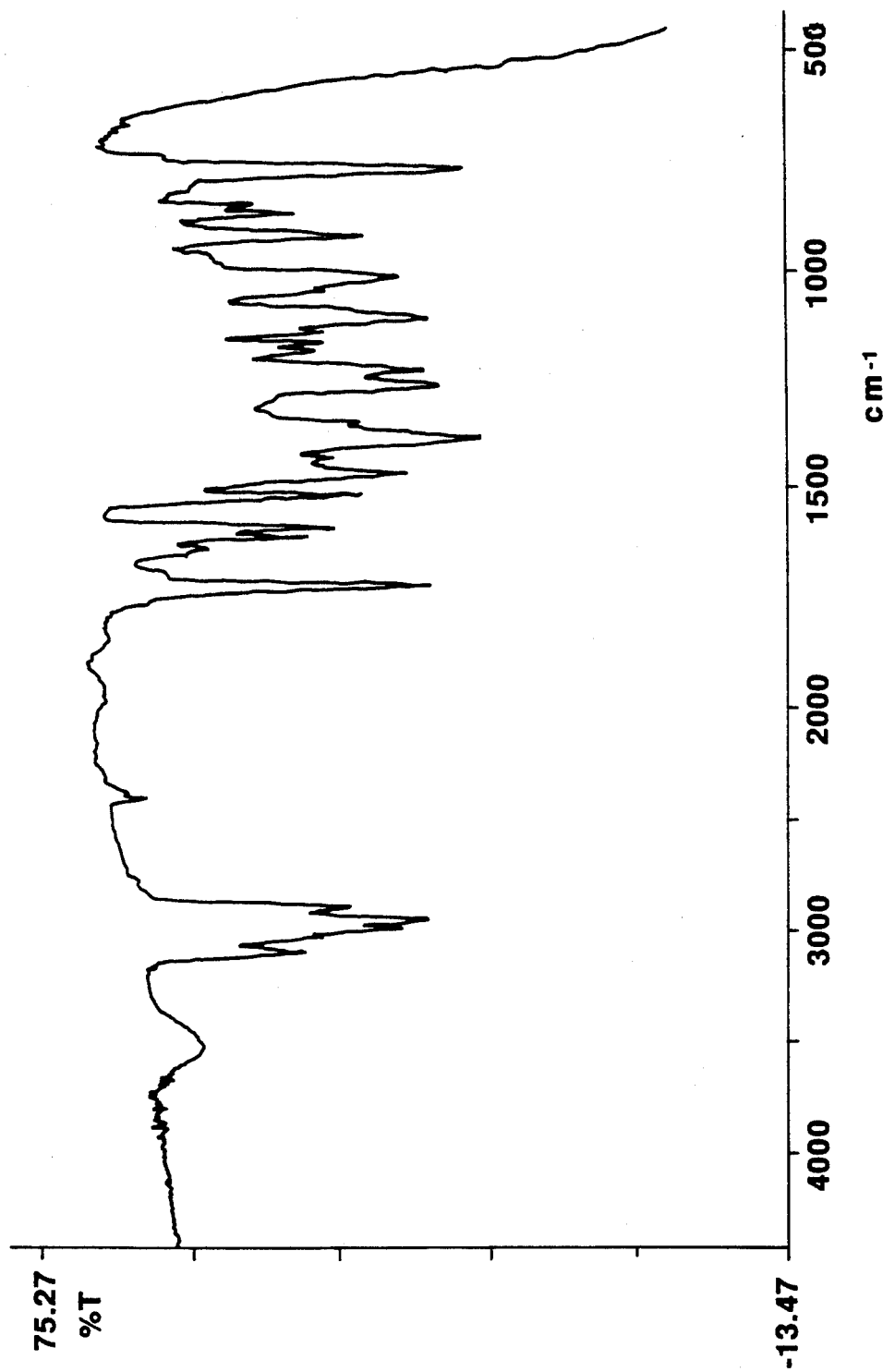
FIG. 2 is an IR absorption spectral chart of another propenyl group-containing naphthalene derivative (compound E obtained in Example 1) according to the present invention.

Preparation of Compound E 479 g of compound D, 1450 g of epichlorohydrin and 1.4 g of cetyltrimethylammonium were placed in a three liter four-necked flask equipped with a condenser, a thermometer and an agitator, followed by agitation under reflux for 3 hours. Thereafter, 22.4 g of NaOH (50% aqueous solution) was dropped under a reduced pressure (80° to 90° C./100 to 130 mmHg). After completion of the dropping, the reaction mixture was aged for 3 hours and filtered, followed by removal of the solvent, further addition of a 10% NaOH aqueous solution to remove hydrolyzing chlorine and washing with water to obtain 583 g of compound E of the following formula with an epoxy equivalent of 232 (theoretical: 223) at a yield of 91%. The IR absorption spectra are shown in FIG. 2. The attributions of NMR spectra are shown below.

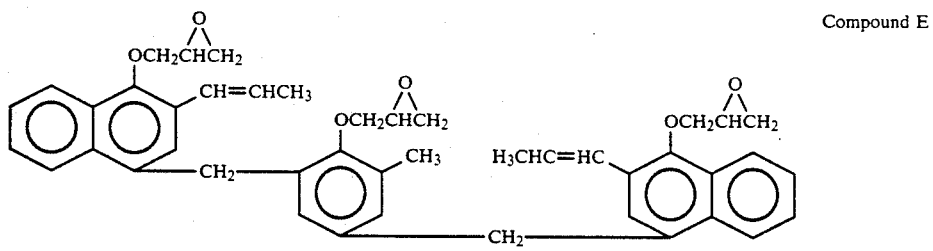

Compound E

NMR spectra (solvent: (CD$_3$)$_2$CO, ppm(δ)):

1.9-2.2: —[C$_6$H$_2$]—$\overset{\text{CH}_3}{|}$, —CH=CH—C$\underline{H}_3$ 2.65: —C$\underline{H}$—$\overset{O}{\overset{/\,\backslash}{}}$CH$_2$ 3.2: —C$\underline{H}$—$\overset{O}{\overset{/\,\backslash}{}}$CH$_2$ 3.6: —C$\underline{H}_2$—

4.0: —C$\underline{H}_2$—CH—$\overset{O}{\overset{/\,\backslash}{}}$CH$_2$ 6.8-8.4: —[C$_6$$\underline{H}_2$], [C$_{10}$$\underline{H}_5$], —C$\underline{H}$=C$\underline{H}$—CH$_3$

EXAMPLE 2

Figure 3:
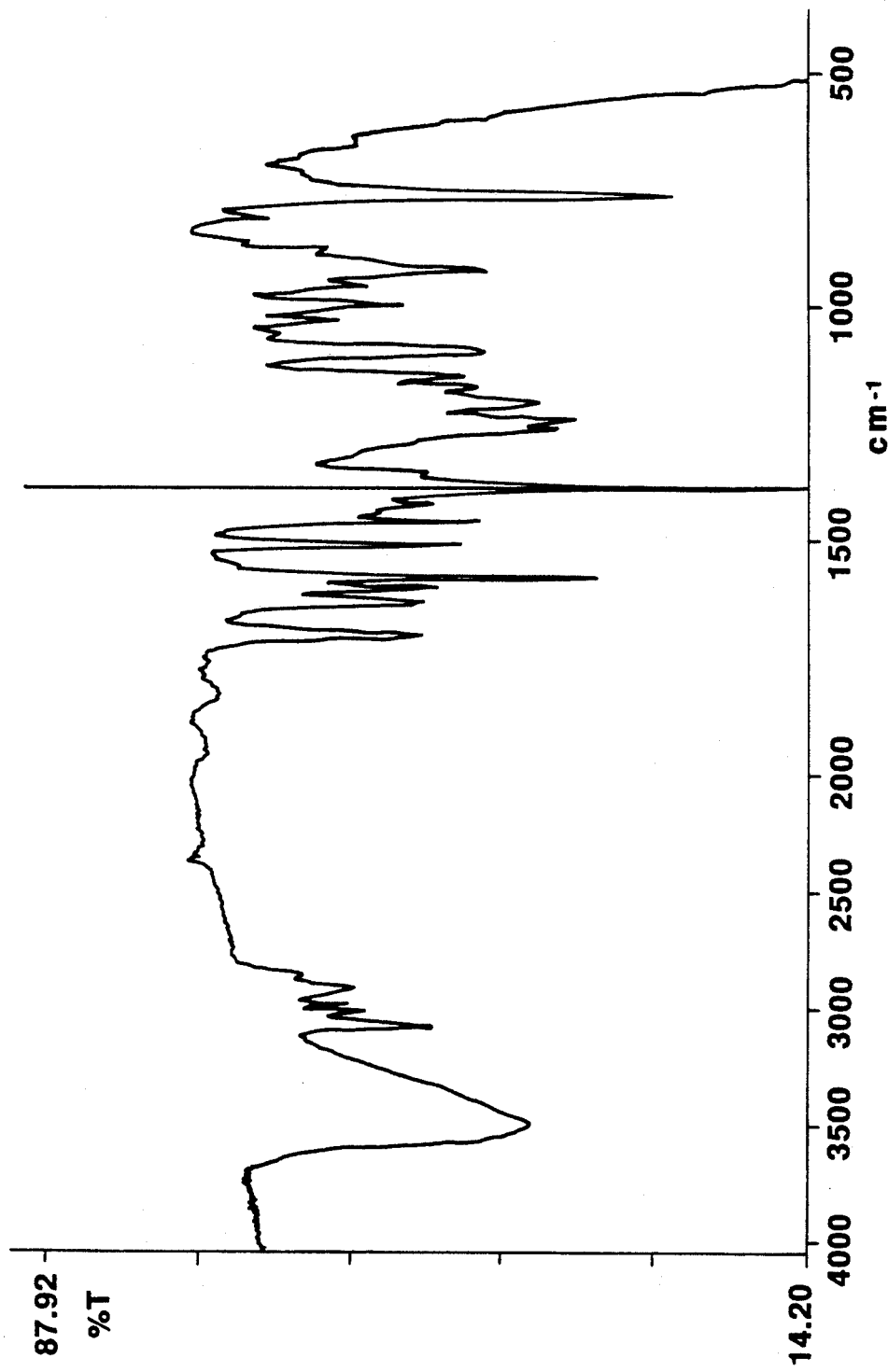
FIG. 3 is an IR absorption spectral chart of an allyl group-containing naphthalene derivative (compound F obtained in Example 2) according to the present invention.

The general procedure for compound C was repeated using 400 g of the compound B, 88.4 g of 37% HCHO and 2.4 g of KOH, thereby obtaining 365 g of compound F of the following formula with a OH equivalent of 199 (theoretical: 190) at a yield of 88%. The compound F was identified by NMR and IR analyses. The IR absorption spectra are shown in FIG. 3. The attributions of NMR spectra are shown below. In the same manner as in Example 1, there were prepared compounds G and H of the following formulas.

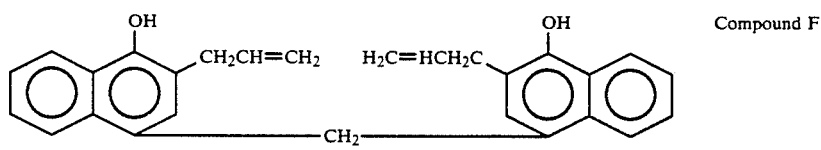

Compound F

NMR spectra (solvent: (CD$_3$)$_2$CO, ppm(δ)):

2.8-3.2: —C$\underline{H}_2$—

3.2-3.7: —CH$_2$—CH=CH$_2$ 4.2-4.8: —C$\underline{H}_2$—CH=CH$_2$ 5.2-6.0: —CH$_2$—C$\underline{H}$=CH$_2$ 6.2-8.2: [C$_{10}$$\underline{H}_5$]

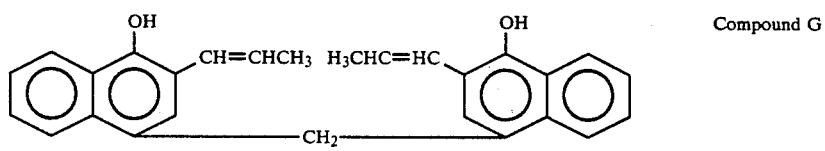

Compound G

OH equivalent 203 (theoretical: 168)

-continued

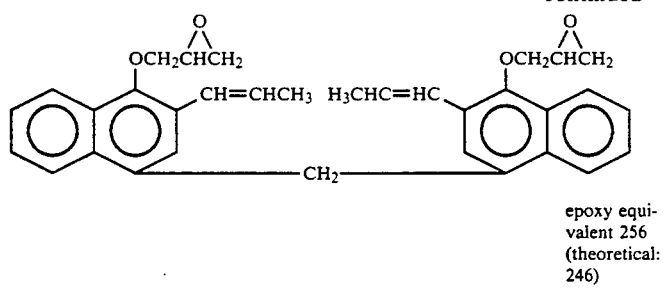

Compound H epoxy equivalent 256
(theoretical: 246)

EXAMPLE 3

400 g of the compound B, 146 g of 2-allylphenol and 264 g of a 37% formaldehyde aqueous solution were placed in an atmosphere of nitrogen in a three liter flask equipped with a condenser, a thermometer and an agitator. While agitating, 7.2 g of KOH was added, followed by reaction for 6 hours under reflux. Thereafter, 8.15 g of oxalic acid, 525 g of toluene and 235 g of o-cresol were further added and were heated and dehydrated for 2 hours under reflux of toluene. After 2 hours, the toluene was removed under reduced pressure, followed by reaction at 150° C. for 1 hour. Thereafter, the reaction product was cooled and diluted with methyl isobutyl ketone, followed by washing with water and removal of the solvent by distillation to obtain 748 g of compound I of the following formula with a OH equivalent of 160 (theoretical: 153) at a yield of 90% based on the compound B. The compound I was identified by NMR and IR analyses. In the same manner as in Example 1, there were prepared compounds J and K of the following formulas.

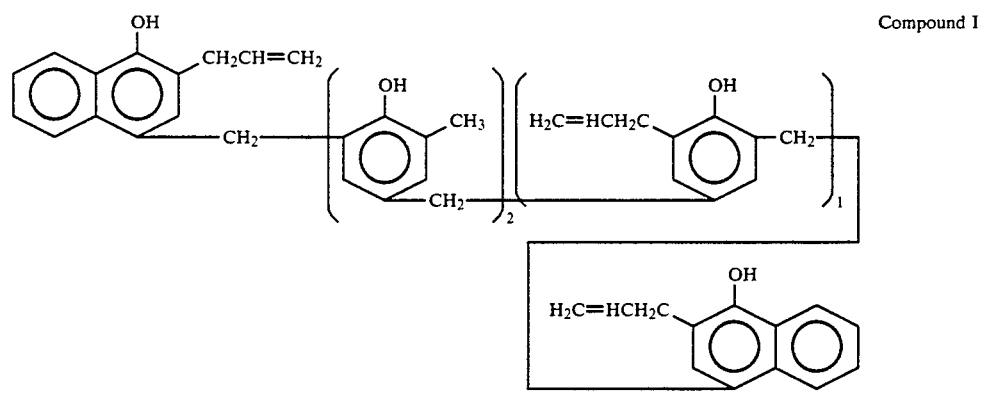

Compound I

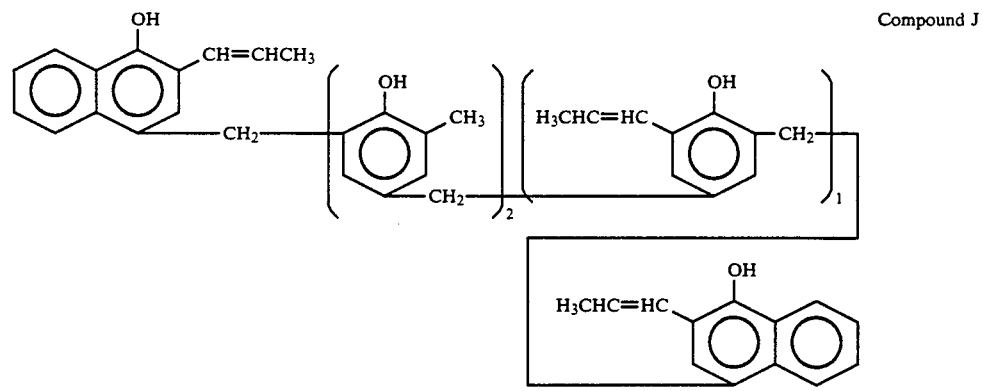

Compound J

OH equivalent 163
(theoretical: 153)

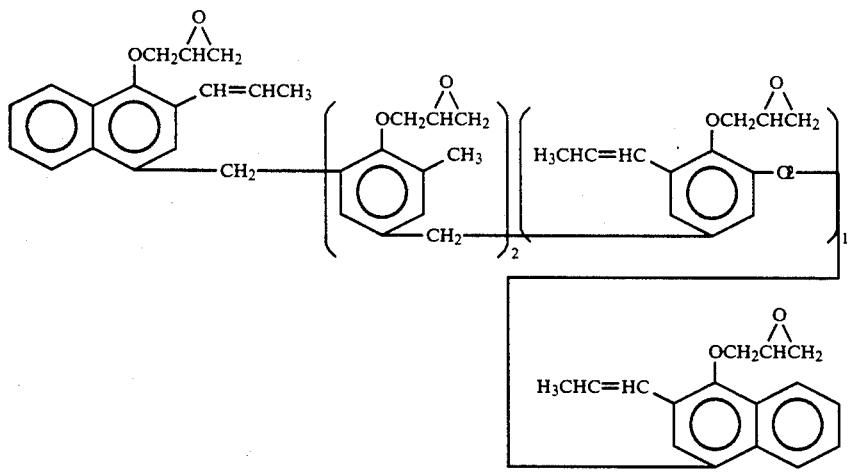

Compound K epoxy equivalent
215 (theoretical: 208)

EXPERIMENT 38.0 parts by weight of compound E of the present invention and 35 parts by weight of N,N'-4,4'-diphenylmethane bismaleimide were provided along with ingredients indicated in Table 1. The resultant mixture was uniformly melted and mixed by means of hot two rolls to obtain thermally curable resin composition I. For comparison, compound L of the following formula was prepared, followed by repeating the above procedure except that compound E was used instead of compound D, thereby obtaining thermally curable resin composition II.

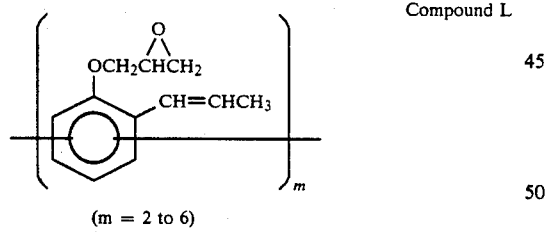

Compound L (m = 2 to 6)

These thermally curable resin compositions were subjected to the following tests (a) to (d). The results are also shown in the Table.

(a) Spiral flow value

A mold as prescribed in the EMMI standards was used and the value was determined at 175° C. at a pressure of 70 kg/cm$^2$.

(b) Mechanical strength (bending strength and flexural modulus)

A 10×4×100 mm bar was made by a method as prescribed in JIS-K6911 under conditions of 175° C., 70 kg/cm$^2$ and a molding time of 2 minutes, and post-cured at 180° C. for 4 hours, followed by measurement at 25° C.

(c) Glass transition temperature

A 4 mm $\phi$×15 mm test piece was used and the transition temperature was measured by heating at a rate of 5° C./minute by means of a dilatometer.

(d) High temperature and high humidity environmental test

A 50 mm $\phi$×3 mm test piece was allowed to stand under conditions of 121° C. and 2 atmospheric pressures for 24 hours, after which its water absorption was measured.

TABLE

| Thermally Curable Resin Composition | I | II |
|---|---|---|
| Composition (parts by weight): | | |
| N,N'-4,4'-diphenylmethane bismaleimide | 35.0 | 35.0 |
| Reaction product: | | |
| compound E | 38.0 | |
| compound L | | 38.0 |
| Phenolic resin (OCN7000) | 15.0 | 15.0 |
| Triphenylphosphine | 0.8 | 0.8 |
| Curing catalyst | 4.0 | 3.0 |
| Dicumyl peroxide | 0.45 | 0.45 |
| Quartz powder | 270.0 | 270.0 |
| γ-glycidoxypropyltrimethoxysilane | 0.8 | 0.8 |
| Wax E | 0.8 | 0.8 |
| Flame retardant | 8.0 | 8.0 |
| Aid for flame retardancy | 8.0 | 8.0 |
| Carbon black | 1.0 | 1.0 |
| Test results: | | |
| Spiral flow (cm) | 70.0 | 50.0 |
| Bending strength (kg/cm$^2$ at 25° C.) | 14.2 | 12.2 |
| Glass transition temperature (°C.) | 198 | 190 |
| Water absorption (%) | 0.68 | 0.90 |

Curing catalyst: melt mixture of DBU:TD2131=2:8
DBU: diazabicycloundecene
OCN7000: product of Nippon Kayaku Co., Ltd.
TD2131: phenol novolac resin
(product of Dainippon Inks Co., Ltd.)

From the results of the above Table, the curable resin composition comprising the naphthalene derivative of the present invention has the fluidity better than obtained from the naphthalene ring-free composition, and is able to provide a cured product which has a higher bending strength, a higher glass transition temperature and a lower water absorption.

Thus, the allyl or propenyl group-containing naphthalene derivatives of the present invention exhibit good working properties and are highly reactive with other epoxy resins, phenolic resins, maleimide resins and the like. In addition, the cured products obtained from compositions comprising the derivatives have good heat resistance and mechanical strength at high temperatures and are resistant to heat deterioration over a long term with a low water absorption and a high degree of hardness. Thus, the derivatives of the invention are effectively utilizable as an ingredient of various resin compositions and also as an modifier for various resins.

What is claimed is:

1. A naphthalene derivative of the following formula (1) having at least two allyl or propenyl groups

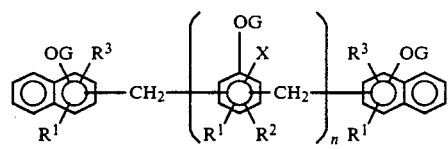

wherein each G represents a hydrogen atoms or

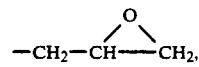

$R^1$'s independently represent a hydrogen atom or an unsubstituted or substituted monovalent hydrocarbon group having from 1 to 6 carbon atoms, $R^2$'s independently represent a hydrogen atom, an allyl group or a propenyl group, $R^3$ represents an allyl group or a propenyl group, X represents a hydrogen atom or a halogen atom, and n is an integer of from 0 to 6.

2. The derivative according to claim 1, wherein each G represents a hydrogen atom whereby a phenolic derivative is obtained.

3. The derivative according to claim 1, wherein at least one of G's is a glycidyl group whereby an epoxidized derivative is obtained.

* * * * *